(12) United States Patent
Chen

(10) Patent No.: US 6,210,425 B1
(45) Date of Patent: Apr. 3, 2001

(54) COMBINED IMAGING AND PDT DELIVERY SYSTEM

(75) Inventor: James C. Chen, Bellevue, WA (US)

(73) Assignee: Light Sciences Corporation, Issaquah, WA (US)

( * ) Notice: Subject to any disclaimer, the term of this patent is extended or adjusted under 35 U.S.C. 154(b) by 0 days.

(21) Appl. No.: 09/350,258

(22) Filed: Jul. 8, 1999

(51) Int. Cl.$^7$ .................................................. A61N 5/00
(52) U.S. Cl. ............................ 607/88; 607/90; 600/439; 600/436
(58) Field of Search .............................. 607/88–90, 92, 607/93; 600/407, 410, 411, 425, 427, 436, 437, 439; 606/2, 9, 13, 17

(56) References Cited

U.S. PATENT DOCUMENTS

| | | | |
|---|---|---|---|
| 4,337,759 | 7/1982 | Popovich et al. | 126/438 |
| 5,042,494 | 8/1991 | Alfano | 128/665 |
| 5,404,869 | 4/1995 | Parkyn, Jr. et al. | 126/699 |
| 5,441,531 | 8/1995 | Zarate et al. | 607/90 |
| 5,806,955 | 9/1998 | Parkyn, Jr. et al. | 362/31 |
| 5,851,181 | * 12/1998 | Talmor | 600/407 |
| 5,860,967 | * 1/1999 | Zavislan et al. | 606/9 |
| 5,944,748 | * 8/1999 | Mager et al. | 607/88 |

OTHER PUBLICATIONS

Program/Proceedings: American Society of Clinical Oncology. Thirty–Fifth Annual Meeting. Abstract #418. vol. 18. May 15–18, 1999. Atlanta, Georgia. P. 111.

\* cited by examiner

Primary Examiner—Linda C. M. Dvorak
Assistant Examiner—Bryan Yarnell
(74) Attorney, Agent, or Firm—Ronald M. Anderson

(57) ABSTRACT

A system having a plurality of light sources that emit light focused to treat an internal treatment site at a location determined using an imaging device that is integrally mounted in a housing with the plurality of light sources. The imaging device may include, for example, either an ultrasonic transducer or a gamma probe that produces a signal suitable for displaying an image of the internal treatment site. The image thus displayed enables the location, shape, extent, and depth of the internal treatment site to be determined so that an operator can correctly position the housing in which the imaging device and light sources are disposed. Each light source is provided with either a conventional refractive lens or a totally internally reflective (TIR) lens that directs and focuses the light at the appropriate depth within a patient's body. In addition to locating the internal treatment site, the imaging device can be employed to monitor the status of the treatment site during the course of light therapy and thus enables modification of the therapy as appropriate to adjust for changes in the shape and size of the internal treatment site.

28 Claims, 7 Drawing Sheets

COMBINED IMAGING AND PDT DELIVERY SYSTEM

FIELD OF THE INVENTION

This invention generally relates to apparatus and a method to identify an internal treatment site within a patient's body for administration of light therapy, and more specifically, to the use of an imaging device to locate the internal treatment site so that non-invasive light therapy can be administered more accurately to the treatment site.

BACKGROUND OF THE INVENTION

Photodynamic therapy (PDT) has proven to be very effective in destroying abnormal tissue such as cancer cells. In this therapy, a photosensitizer agent having a characteristic light absorption waveband is first administered to the patient, typically either orally or by injection. Abnormal tissue in the body is known to selectively absorb certain photosensitizer agents to a much greater extent than normal tissue, e.g., tumors of the pancreas and colon may absorb two to three times the volume of these agents, compared to normal tissue. Even more effective selectivity can be achieved using a photoreactive agent that is bound to an antibody, which links with antigens on targeted cells. The cancerous or abnormal tissue that has absorbed or linked with the photosensitizer dye is then destroyed by administering light of an appropriate wavelength or waveband corresponding to the absorption wavelength or waveband of the photosensitizer agent.

To administer PDT to internal cancerous lesions that are not accessible through a natural body orifice, a fiber optic probe is typically inserted either through a needle or through a surgically created opening. The internal cancerous lesions are visually located by imaging the treatment site through the fiber optic system so that light from a laser source can be accurately directed through the optical fiber to destroy the abnormal tissue. Even when the internal treatment site is accessible through natural body orifices, an endoscope is usually required to visualize the lesion and accurately direct the light therapy administered to the treatment site. The invasive placement of an optical fiber probe or endoscope at an internal treatment site exposes a patient to potential risks associated with bleeding, infection, and the use of anesthesia and sedation.

Clearly, it would be preferable to administer PDT to an internal treatment site using a non-invasive approach in which light from an external source is applied to the intact dermal layer overlying an internal treatment site and penetrates the overlying tissue sufficiently to destroy the abnormal cells at the treatment site. The prior art describes the use of externally applied light for PDT, which is typically emitted by lamps, lasers, light emitting diodes (LEDs), and laser diode arrays, but in the past, PDT has been employed primarily to treat relatively superficial cutaneous treatment sites, e.g., for treatment of skin lesions, and generally has not been widely used for treating sub-dermal diseased tissue.

Light of longer wavelengths (e.g., longer than 700 nm) is able to penetrate dermal tissue sufficiently to reach internal treatment sites, where tumors may be disposed. A two photon absorption system for administering PDT to treat metastasized cancer cells is described in commonly assigned U.S. Pat. No. 5,957,960 (U.S. Ser. No. 08/850,909, filed May 5, 1997, which has been allowed). However, this and other systems disclosed in the prior art for administering PDT with an externally applied light source are not particularly useful for targeting specific small and large volume tumors.

One of the problems with administering light therapy to an internal treatment site with an externally applied light source relates to the difficulty in accurately directing the light through the overlying tissue, since the disposition of the internal treatment site is normally not visually apparent to the medical practitioner. However, it is possible to employ various imaging systems to identify the location of abnormal tissue within a patient's body, including its depth below the dermal layer. Suitable imaging systems capable of imaging soft tissue structures to locate internal diseased sites include ultrasound probes and gamma probes. By viewing the images of the patient's internal body structure, it is possible to determine an appropriate position, direction, and depth at which to focus light of an appropriate waveband at a position on the patient's skin. However, it would be inconvenient to implement an imaging procedure to locate a treatment site and then position one or more external light sources to focus on the site thus found. Due to movement of the patient's body (both internal and external) that will typically occur after the imaging procedure is completed, it is likely that the light may be inaccurately focused on the internal treatment site identified by the imaging process. Instead, it would be preferable to provide an integral light therapy device that includes a light source and an imaging probe, so that the light is more accurately focused on and administered to the treatment site identified and located by the imaging probe. In addition, an imaging probe that is an integral part of the apparatus used to administer light therapy can monitor the effects of the light therapy in real time, without interrupting the therapy. It may be particularly important to monitor the status of an internal treatment site during a period of light therapy that extends over several hours, since the therapy may cause changes in the site being treated that should be noted by the medical practitioner.

If an imaging system is used to determine the depth at which light from multiple sources is focused during the administration of PDT, it will also be necessary to provide a mechanism for altering the focal point and/or the direction in which the light is directed. Use of plural light sources will probably be preferable in most cases, since the intensity of the light from a single source passing through tissue overlying the treatment site will be much less than the intensity of the light from all of the plurality of light sources at the point of intersection at the internal treatment site. Accordingly, the adverse impact of the light therapy on normal tissue will be minimized, because the intensity of the light from a single source will be below the threshold necessary to activate the photosensitizer agent, particularly at the lower concentration of the drug in normal tissue. Furthermore, by varying the direction in which light emitted by selected light sources penetrates the patient's body, it should be possible to apply the light therapy at an internal treatment site in conformance with the shape and dimension of the abnormal tissue or tumor. Thus, the light might be directed into the body to encompass an elongate tumor in one patient, and a smaller, more spherical tumor in another patient, or to treat different portions of an irregularly-shaped tumor in yet another patient.

The advantages provided by a system and method for administering light therapy that includes an imaging device are also applicable for rendering light therapy to treat non-oncologic conditions such as atherosclerotic and infectious disease. The imaging probe can provide a much more accurate basis for directing the light therapy at internal sites to destroy diseased tissue or to inhibit the growth of undesirable organisms.

SUMMARY OF THE INVENTION

In accord with the present invention, apparatus is defined for administering light therapy to an internal treatment site within a patient's body. The apparatus includes a housing that supports a light source emitting light within a waveband sufficiently long to penetrate through a dermal layer to an underlying internal treatment site. An imaging probe is also mounted within the housing. The imaging probe is adapted to produce a signal indicative of a location of an internal treatment site within a patient's body for use in producing an image that facilitates positioning the housing to direct the light emitted by the light source toward the internal treatment site.

Also preferably included is a focusing element that focuses the light emitted by the light source onto the internal treatment site. In the preferred embodiments of the apparatus, a plurality of light sources are arranged in either a curved or a linear array. The focusing element is provided to control a direction in which the light emitted by each of the plurality of light sources propagates so that the light travels toward the internal treatment site. This focusing element may comprise either a totally internal reflecting (TIR) lens or a refractive lens (or a combination thereof).

In different embodiments, the imaging probe includes either an ultrasonic probe or a gamma probe. The ultrasonic probe emits an ultrasonic signal adapted to propagate into a patient's body and produces an output signal used for creating an image of the treatment site in response to reflections of the ultrasonic signal from within a patient's body. The gamma probe also produces a signal responsive to gamma rays that is useable for imaging the site.

In one embodiment, the plurality of light sources are arrayed in a circle about the imaging probe. In another embodiment, the imaging probe is disposed adjacent to an end of a linear array of light sources.

Preferably, the light sources include either a plurality of laser diodes, a plurality of light emitting diodes, a plurality of incandescent light bulbs, or a plurality of gas discharge devices. The light emitted by the plurality of light sources is adapted to preferably converge on an internal treatment site, producing a substantially greater total intensity at the site than the intensity of each light source, if measured separately, so that the lower intensity light penetrating the intervening normal tissue has little effect.

The apparatus may also include a display device coupled to the imaging probe. The display device is adapted to display an image of an internal treatment site. In one embodiment, a power supply provides a plurality of intermittent pulses of electrical current to energize the plurality of light sources. These light sources then produce corresponding intermittent light pulses that are directed toward an internal treatment site, thereby reducing a dose of light delivered to normal tissue overlying an internal treatment site.

To change the focus of the plurality of light sources, a plurality of lenses having different focal lengths are provided. A specific one of the plurality of lenses is then selected to focus light emitted by the light source onto an internal treatment site.

Optionally, an auxiliary imaging probe adapted to produce a signal used to image an internal treatment site from a different position on a patient's body than that of the imaging probe disposed inside the housing with the light sources may be included.

A further aspect of the present invention is directed to a method comprising steps that are generally consistent with the description of the functions performed by the elements of the apparatus described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
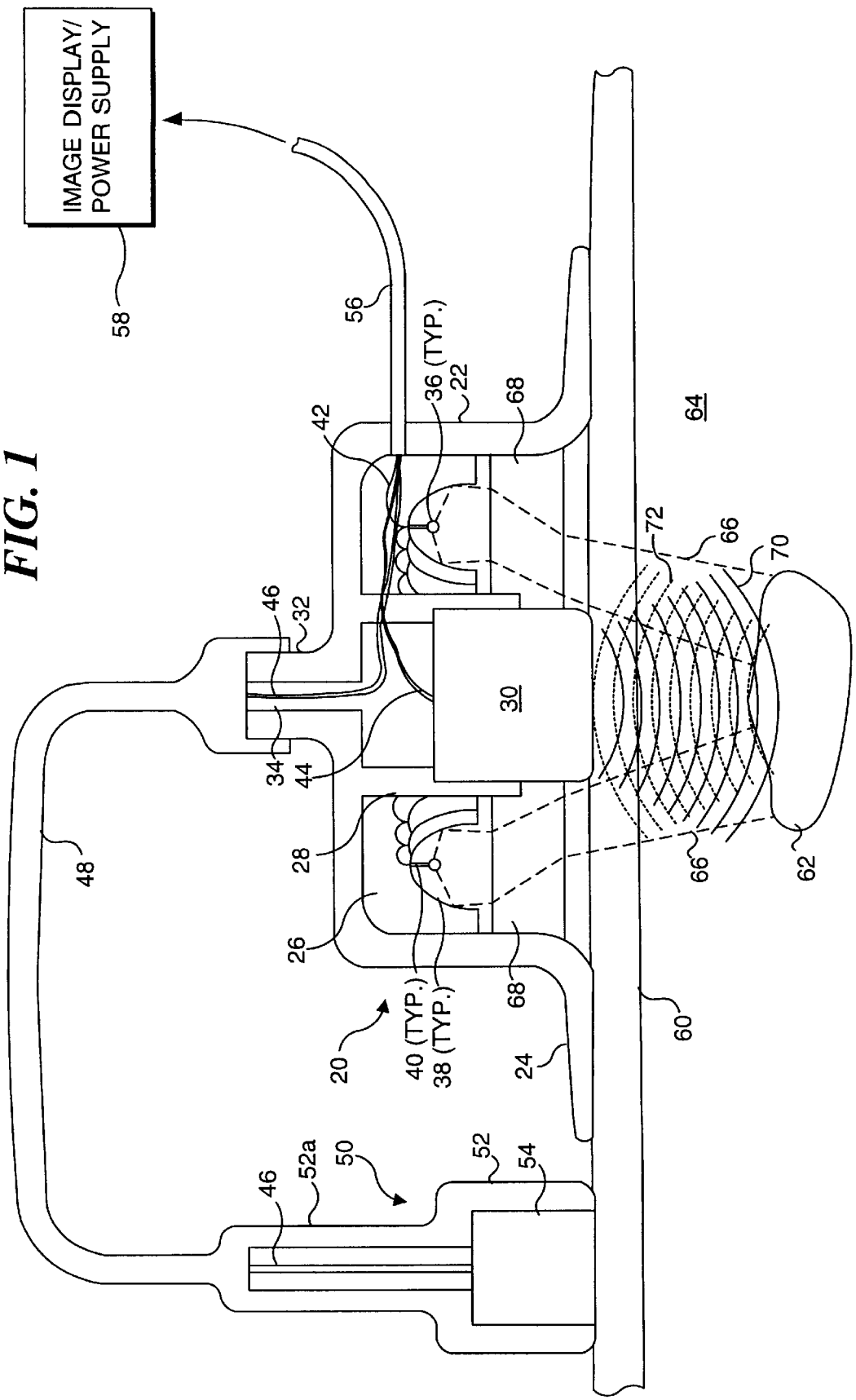
FIG. 1 is a schematic, elevational cross-sectional view of a first preferred embodiment of the present invention that includes a housing in which a plurality of light sources and an imaging probe are mounted, and an auxiliary probe, and showing an internal tumor being administered light emitted by the light sources.

A first embodiment of the present invention is illustrated in FIG. 1. This embodiment includes a therapy head 20 that includes a generally cylindrical-shaped housing 22 around the base of which extends a flange 24. Flange 24 is sufficiently smooth to readily glide over a dermal layer 60 of a patient. Housing 22 defines an interior volume 26. Depending from the center of the housing 22 into interior volume 26 is a generally cylindrical-shaped support 28 within which is mounted an ultrasonic transducer 30. The bottom of ultrasonic transducer 30 is substantially aligned with the lower surface of flange 24 so that when therapy head 20 is brought into contact with a patient's body (not specifically shown), ultrasonic transducer 30 contacts the skin of the patient. While not shown in this view, the gels or creams typically used for improving ultrasonic pulse transfer between an ultrasonic transducer and a patient's body would preferably be applied to the patient's skin to facilitate use of this device and to minimize friction as housing 22 is moved over the skin of the patient while locating an internal treatment site.

Extending upwardly from the center of housing 22 is a generally cylindrical-shaped nipple 32 through which extends a passage 34. The purpose of this passage is explained below.

A plurality of light sources 36 are disposed within housing 22, and in this embodiment, are arranged in a curved array within the annular volume lying between the interior surface of housing 22 and support 28. Preferably, light sources 36 comprise LEDs, although they may alternatively comprise incandescent bulbs, gas discharge devices, laser diodes, various polymeric electroluminescent devices, or other appropriate light emitting sources. Furthermore, light sources 36 preferably emit light within a waveband that includes wave lengths greater than 700 nm to ensure that the light emitted thereby is able to penetrate tissue, into a patient's body, to reach a desired treatment site. The longer the wavelength of the light, the deeper that the light can penetrate through overlying skin and tissue.

In this embodiment, light sources 36 are each disposed at a focal point of one of a plurality of parabolic reflectors 38, which are also arranged in a curved array forming a ring around ultrasonic transducer 30. A relatively small diameter support 40 holds each light source 36 at the focal point of its respective parabolic reflector 38, and leads 42, which carry an electrical current to energize the light sources, extend from each light source through supports 40.

A lead 44 is connected to ultrasonic transducer 30 and is used to supply it electrical current and to convey a signal produced by it, as explained below. A second set of leads 46 extends through passage 34 and into a cable 48 that is fitted around nipple 32 and is connected to an auxiliary ultrasonic probe 50. Ultrasonic probe 50 includes a housing 52, having a handle portion 52a, and both the handle portion and the lower main portion of housing 52 are generally cylindrical in shape. Within the lower portion of housing 52 is disposed an auxiliary ultrasonic transducer 54 that is connected to leads 46, which carry an electrical current to energize it and convey a signal that it produces. Leads 42, 44, and 46 are shield within a cable 56 through which they are conveyed to an image display/power supply 58. The electrical current supplied to energize light sources 36 by the image display/power supply can be continuous, so that the light sources remain energized during the time that the light therapy is being administered, or may be supplied as pulses at a rate of from about ten to 100 pulses/sec.; the resulting pulsing light minimizes the effects of light exposure on normal tissue through which the light passes.

The image display/power supply includes a display screen (not separately shown) on which images produced in response to the signals from ultrasonic transducer 30 and auxiliary ultrasonic transducer 54 are displayed. These images are useful in determining a location, extent, and depth of a treatment site to which PDT is to be administered using light sources 36. The ability to view the treatment site and to determine its depth and extent is extremely helpful to medical practitioners for properly positioning a plurality of light sources 36 so that the light emitted thereby accurately is directed toward the treatment site and extends to the appropriate depth and in the desired direction to apply light therapy expected to destroy abnormal tissue and to treat other medical conditions receptive to PDT.

To administer PDT to a patient, for example, to destroy a tumor 62, which is disposed internally within a patient's body below dermal layer 60, a photoreactive agent is administered to the patient, and sufficient time is allowed to pass to enable the photoreactive agent to be selectively absorbed by the abnormal tissue comprising tumor 62. Suitable photoreactive agents include indocyanine green, toluidine blue, porphyrins, phthalocyanines, prodrugs such as aminolevulinic acid, chlorins, texaphyrins, purpurins, benzoporphyrins, phenothiazines, and other photoactive dyes and compounds. In addition to the photoreactive agents listed above, it is also contemplated that a targeted photoreactive agent can be used to more selectively bind to the abnormal tissue within tumor 62, since a much lower dose of a targeted photoreactive agent can be used than would typically be required for a non-targeted type photoreactive agent. The photoreactive agent chosen can be administered via an interstitial injection, which is generally suitable for discrete lesions or tumors such as tumor 62, or via an intravenous or intra-arterial injection. A targeted photoreactive agent typically includes antibodies that are targeted to specifically link with antigens on abnormal tissue or malignant cell organelles with a patient's body. Details relating to such targeted photoreactive agents are disclosed in commonly assigned U.S. patent application Ser. No. 09/078,329, filed May 13, 1998, entitled "Controlled Activation of Targeted Radionuclides;" Ser. No. 60/116,234, filed Jan. 15, 1999, entitled "Targeted Transcutaneous Cancer Therapy," and Ser. No. 60/116,235, filed on Jan. 15, 1999, and entitled "Noninvasive Vascular Therapy." The disclosure, including specification and drawings of each of these three pending patent applications is hereby specifically incorporated herein by reference.

The photoreactive reagent that has been absorbed, and/or specifically targeted at the abnormal tissue in tumor 62 and consequently bound thereto has a characteristic light absorption waveband corresponding to the waveband of light emitted by light sources 36. By using ultrasonic transducer 30, as noted above, it is possible for a medical practitioner to image tumor 62, thereby determining its extent, and its depth below the patient's dermal layer. Having determined the appropriate depth and the direction in which light emitted by light sources 36 should be directed, a medical practitioner inserts an appropriate refractive lens 68 into the housing. Lens 68 is generally annular in shape and includes one or more elements (not separately shown) having upper and lower surfaces appropriately shaped to refract light in a direction chosen so that the light emitted by light sources 36 is directed onto tumor 62 at the depth at which it was found within the patient's body, below dermal layer 60. It is contemplated that a plurality of different focal length refractive lenses 68 will be provided for use with therapy head 20. The medical practitioner can then select an appropriate lens from among these different refractive lens for use in the therapy head. Light emitted by light sources 36 can thus be employed to render light therapy over different size and shape internal treatment sites, and at different depths within a patient's body. Auxiliary ultrasonic probe 50 is used to more accurately determine the extent, shape, and depth of a treatment site within a patient's body, to enable the medical practitioner to correctly choose the appropriate lens 68 and properly position therapy head 20 over a treatment site such as tumor 62.

While most of the examples of the internal treatment sites shown in the attached drawing Figures illustrate abnormal tissue comprising one or more tumors, it should be understood that other types of diseases can also be treated using the present invention. Specifically, light therapy can be administered for treating non-oncologic conditions, such as atherosclerotic and infectious diseases. Such non-oncologic conditions should benefit from the use of an imaging device for locating and visually perceiving the depth and the extent of the diseased soft tissue for treatment with the light therapy.

Although the light emitted by light sources such as LEDs is of relatively low intensity, by appropriately directing the light to optimally deliver it onto a treatment site, the efficacy of the PDT is greatly improved. In addition, use of ultrasonic transducer 30 (and auxiliary ultrasonic probe 50) should enable the medical practitioner to monitor the condition of the treatment site as the PDT is being administered; as tumor 62 or other abnormal tissue at the treatment site is destroyed, and the size of the treatment site decreases, appropriate changes can be made in the direction and focus of the light being administered by selectively replacing refractive lens 68 with a different refractive lens having focal length and directional properties that better administer light therapy to the treatment site in its diminished size. The ability to monitor the status of the treatment site can also be helpful in determining the extent of the therapy required, since it would be desirable to terminate the administration of PDT as soon as practical, to ensure that only the light therapy required to completely destroy the abnormal tissue is administered. Also, the medical practitioner, by using the ultrasonic probe to continuously monitor the condition of the treatment site and evaluate the efficacy of the treatment, may determine whether additional photoreactive agent should be administered to the patient.

Figure 2:
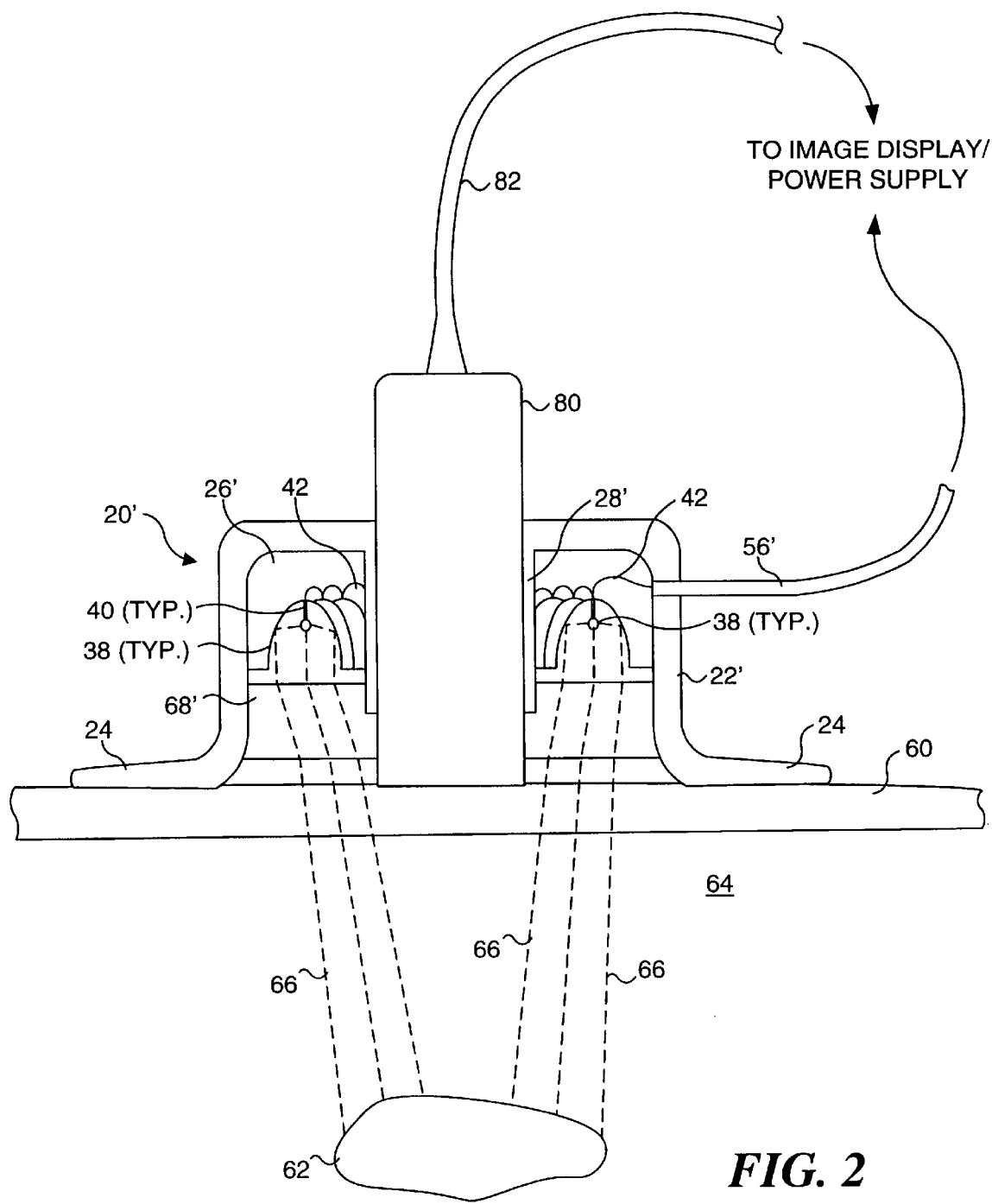
FIG. 2 is a schematic, elevational cross-sectional view of a second preferred embodiment of the present invention in which a gamma probe is being used for imaging an internal tumor.

A second embodiment of the present invention is illustrated in FIG. 2. Since many of the elements of this second embodiment and of other embodiments discussed below function in a manner virtually identical to those corresponding elements of the first embodiment, the same reference numerals have been used, but a prime ('), double prime ("), and/or a triple prime ('") designation has been applied to indicate differences in shape and minor differences in function. Thus, FIG. 2 illustrates a therapy head 20' that supports a generally cylindrical-shaped gamma probe 80. Gamma probe 80 is somewhat longer in length than ultrasonic transducer 30 (shown in FIG. 1). In addition, gamma probe 80 is coupled to the image display/power supply through a cable 82, but the image formed is of a different quality than that provided by the ultrasonic transducer, as will be understood by those of ordinary skill in the art. A housing 22' in this embodiment has a slightly different shape than housing 22 to accommodate gamma probe 80, as does a support 28' in which gamma probe 80 is mounted. The lower end of gamma probe 80 is positioned to contact the outer surface of dermal layer 60. Prior to using gamma probe 80 to form an image, an appropriate gamma emitter is administered to the patient, and selectively absorbed or taken up by tissue at the internal treatment site. Suitable gamma emitters include a variety of radio-pharmaceuticals, such as technetium compounds, antibody labeled radionuclides, gamma emitting liposomes, and radio-labeled hormones. Gamma rays emitted by the radio-pharmaceutical administered to the patient are used by gamma probe 80 to produce a signal suitable to image tumor 62 (or other internal treatment site) to which PDT is to be administered. It should also be noted that auxiliary ultrasonic probe 50 is not used in connection with this second embodiment.

A refractive lens 68' of different focal length than refractive lens 68 is employed in housing 20' to focus light rays 66 at a different depth within sub-dermal regions 64 so that the light rays focus on tumor 62. It should also be noted that a cable 56' provided in the second embodiment shown in FIG. 2 contains only leads 42 that provide electrical current to light sources 36, cable 82 being provided to convey power to gamma probe 80, and to convey a signal produced by the gamma probe 80 to the image display/power supply. It should be noted that the term "imaging device" as used in the claims that follow is intended to generically refer to the gamma probe, the ultrasonic transducer, and to any other device that produces a signal that is useable to produce an image corresponding to the internal treatment site, on a suitable display device.

Figure 3:
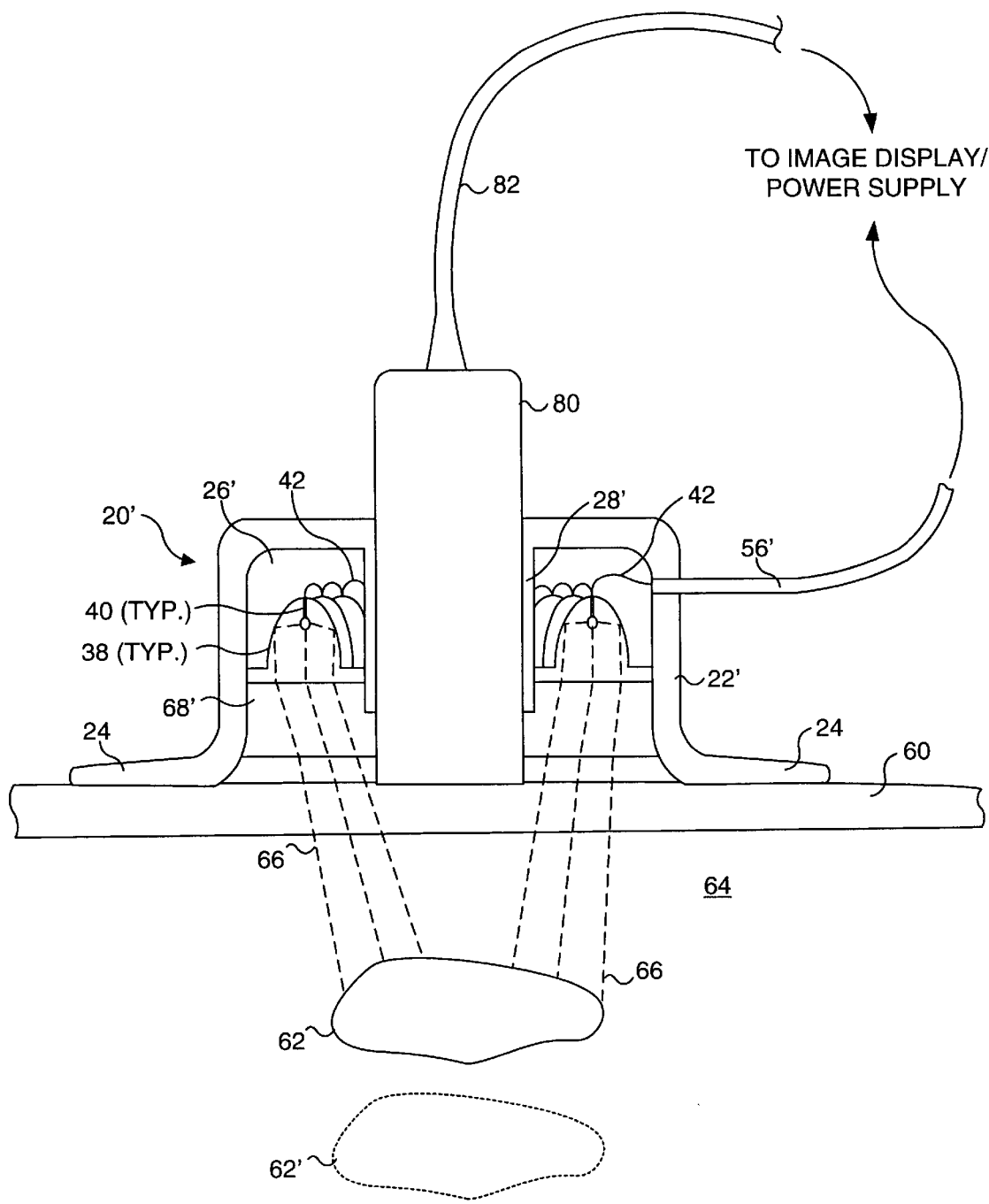
FIG. 3 is a schematic, elevational cross-sectional view of the second preferred embodiment illustrating how the invention is employed to focus light onto tumors disposed at different depths within a patient's body.

FIG. 3, which is identical to FIG. 2, also illustrates the components of therapy head 20'. However, in FIG. 3, a tumor 62' disposed at a relatively shallower depth compared to tumor 62 is illustrated (a dotted line defines the shape and disposition of tumor 62). Tumor 62' is most effectively treated by replacing lens 68' with a different refractive lens that focuses light 66 on tumor 62 at its shallower depth. By using different refractive lenses that focus light rays 66 at different depths and in different directions within the patient's body, it is possible to obtain a light distribution pattern appropriate to treat tumors and other treatment sites having various shapes and sizes, at different depths. Gamma probe 80 in therapy head 20' enables the medical practitioner to visually perceive the treatment site and to determine its extent, shape, and depth in much the same way as was described in regard to ultrasonic transducer 30, which is used in the first embodiment.

Figure 4:
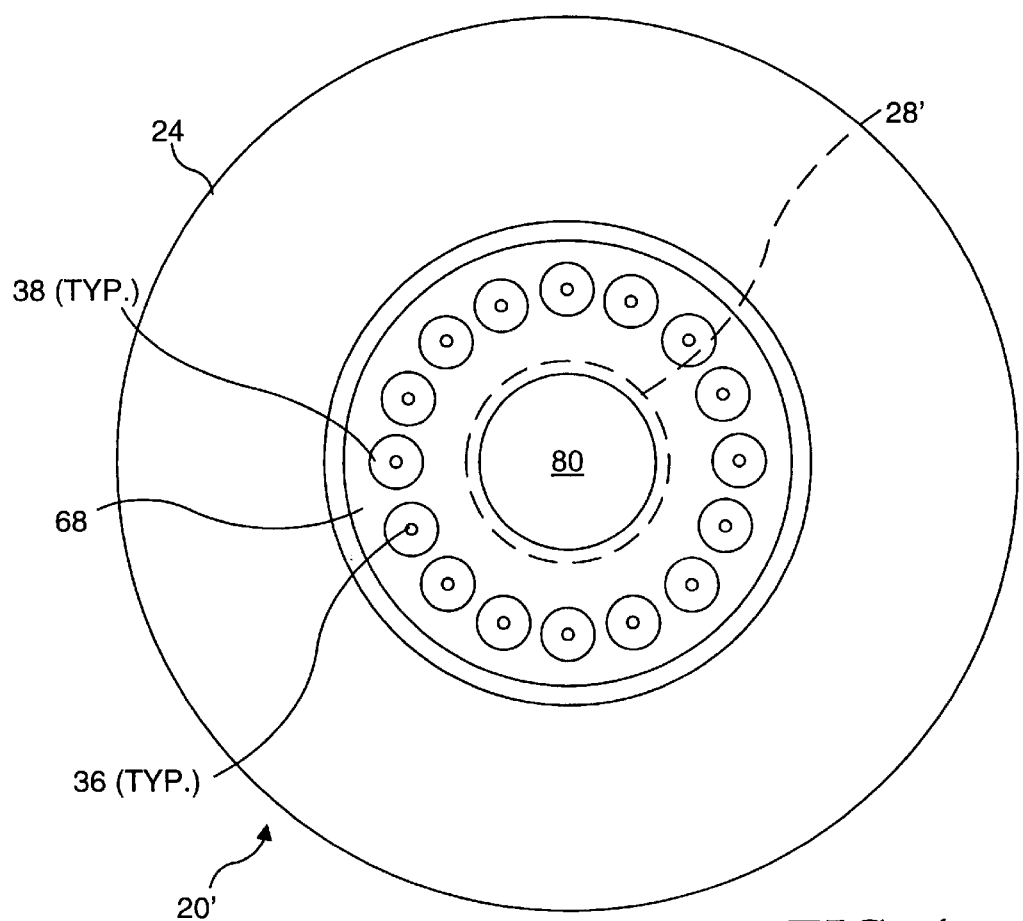
FIG. 4 is a bottom plan view of the first and the second preferred embodiments of the present invention.

FIG. 4 illustrates the spaced-apart array of light sources 36 and parabolic reflectors 38 around gamma probe 80. It is also contemplated, although not shown, that other shaped arrays of light sources 36 and parabolic reflectors can be used. For example, it is relatively easy to imagine a therapy head in which the array of light sources and parabolic reflectors are arranged in an oval shape about one or more gamma probes or ultrasonic transducers. It would thus be possible to select a therapy head having an appropriate shape to administer light therapy to a treatment site having a corresponding shape. Since the ultrasonic transducer or gamma probe provided in the therapy head enables the medical practitioner to visually perceive the shape of the treatment site, selecting the appropriate shape therapy head (light source array) for administering treatment and monitoring the status of the treatment while it is ongoing can readily be accomplished using the present invention.

Figure 5:
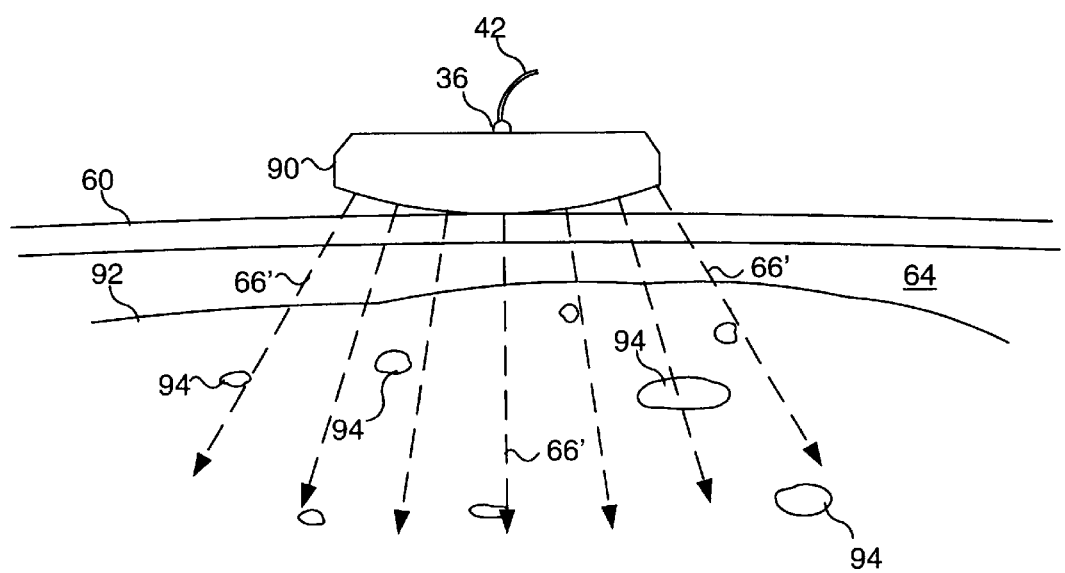
FIG. 5 is a schematic side view showing a cross section of a liver and the dispersion of light effected by a totally internally-reflecting lens to treat a plurality of small tumors within the liver.

Instead of using an annular refractive lens to focus light emitted by light sources 36, it is also possible to use other devices. FIG. 5 illustrates how a totally internally-reflecting lens 90 can be employed to focus light emitted by light source 36 through dermal layer 60 and into a sub-dermal portion of a patient's body, for administering treatment to an internal organ 92, such as the liver, in which a plurality of relatively smaller tumors 94 are disposed. As shown in FIG. 5, light rays 66' diverge to encompass a relatively larger area to facilitate administration of light therapy to the plurality of tumors 94. Details of TIR (Totally Internally-reflecting) lens 90 are discussed below.

Figure 6:
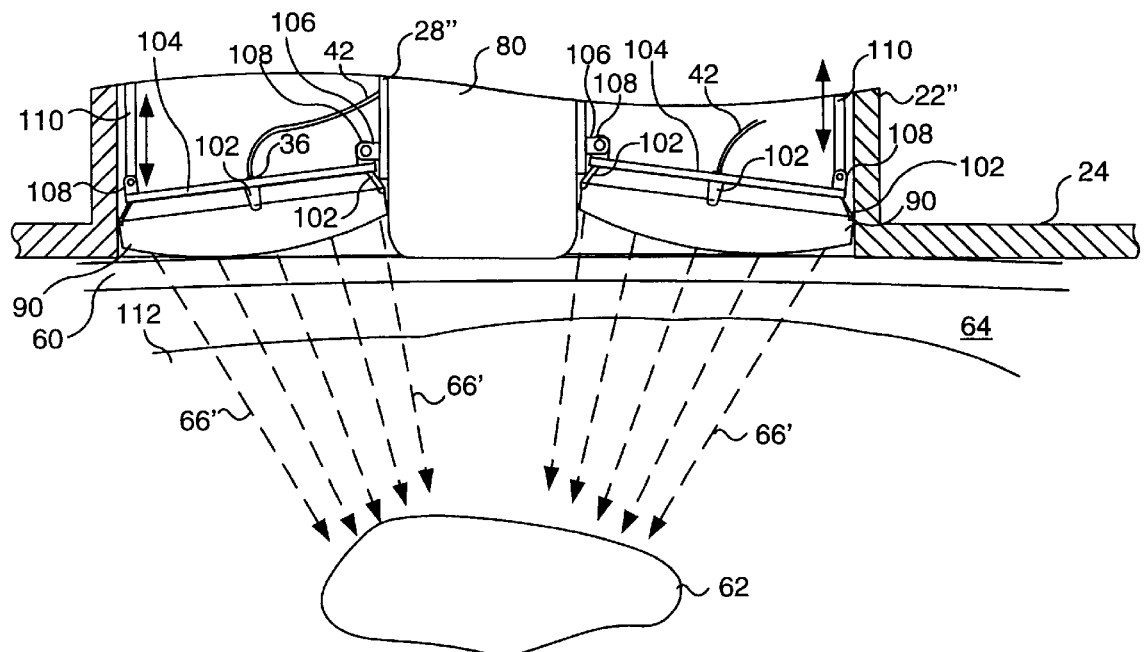
FIG. 6 is a partial schematic, elevational cross section of third preferred embodiment that includes a plurality of a totally internally-reflecting lens that can be pivoted to direct light onto an internal treatment site at different depths within a patient's body.

In FIG. 6, a therapy head 22" is illustrated in which a plurality of TIR lenses 90 are used to focus light rays 66' onto internal tumor 62. While it is also possible to use replaceable TIR lenses having different internal configurations for changing the focus of the light and direction of light rays that have passed through the TIR lenses, the direction at which the light rays are directed can be mechanically changed, as shown in FIG. 6. In therapy head 22", TIR lenses 90 are each pivotally supported, using tabs 102 that folded downwardly, around the periphery of the TIR lenses to clamp on them and are attached to a support ring 104, which is provided for each TIR lens. Adjacent a cylindrical support 28" and adjacent the interior surface of housing 22", support ring 104 includes pivot tabs 108. Each pivot tab disposed adjacent support 28" is pivotally connected to a pivot support 106 that extends radially outwardly from support 28". Each pivot tab disposed adjacent the interior surface of housing 22" is pivotally connected to a rod 110 that moves vertically up and down, and is controlled by rotation of a ring (not shown) disposed around the outer circumference of housing 22", or by another suitable mechanism to move rods 110 to adjust the relative dispositions of each of TIR lenses 90 within the housing. As rods 110 move downwardly within housing 22", the outer portion of each of TIR lenses 90 are pivoted downwardly about their respective pivot supports 106, causing the light that passes through the TIR lenses to be directed more toward the central longitudinal axis of gamma probe 80 or housing 22". Thus, TIR lenses 90 are pivoted to focus the light emitted by light sources 36 onto tumor 62 or other internal treatment site as determined by gamma probe 80 (or by ultrasonic transducer 30). While the embodiment shown in FIG. 6 includes the gamma probe rather than the ultrasonic transducer, it will be understood that gamma probe 80 can be replaced with ultrasonic transducer 30 to create yet another embodiment in which the image formed in response to the signal produced as a function of the reflected ultrasonic waves is used for determining the location, extent, shape, and depth of the treatment site to which the light therapy is to be administered.

Figure 7:
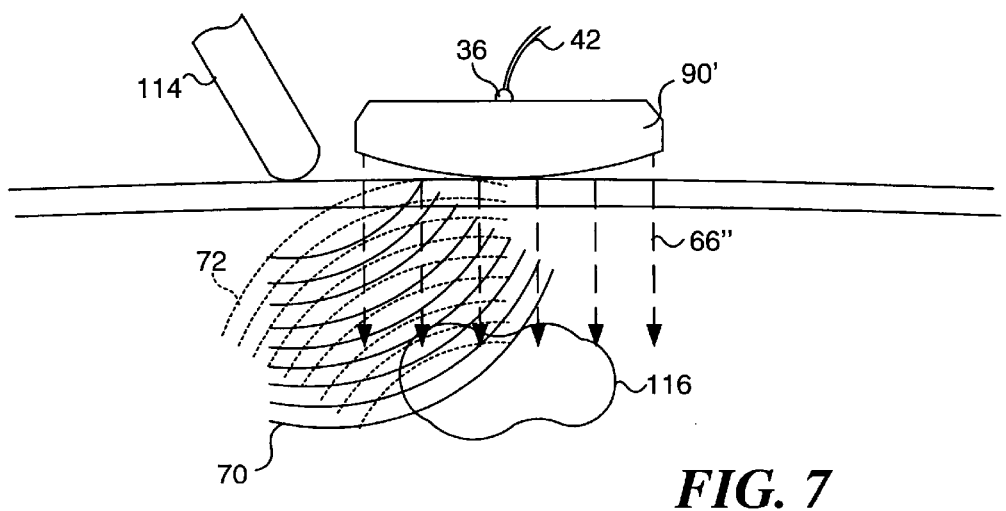
FIG. 7 is a schematic, side elevational view showing a cross-sectional view of a tumor to illustrate how an auxiliary ultrasonic probe is used to assess the efficacy of light therapy during the course of the therapy.

As illustrated in FIG. 7, it is also contemplated that an auxiliary ultrasonic probe 114 can be used in connection with a TIR lens 90'. Although only single such lens is illustrated in FIG. 7, it will be understood that a plurality of TIR lenses 90' and light sources 36 can be included within housing 22 (FIG. 1) that includes ultrasonic transducer 30. FIG. 7 illustrates how TIR lens 90' focuses light rays 66" along generally parallel paths, rather than along paths that converge on a focal point. Auxiliary ultrasonic probe 114 is used for determining the location of the treatment site, and monitoring its depth and extent during the administration of light therapy. Since light rays 66" travel generally along parallel paths, they can be used for treating a somewhat larger area than light rays that converge.

Figure 8:
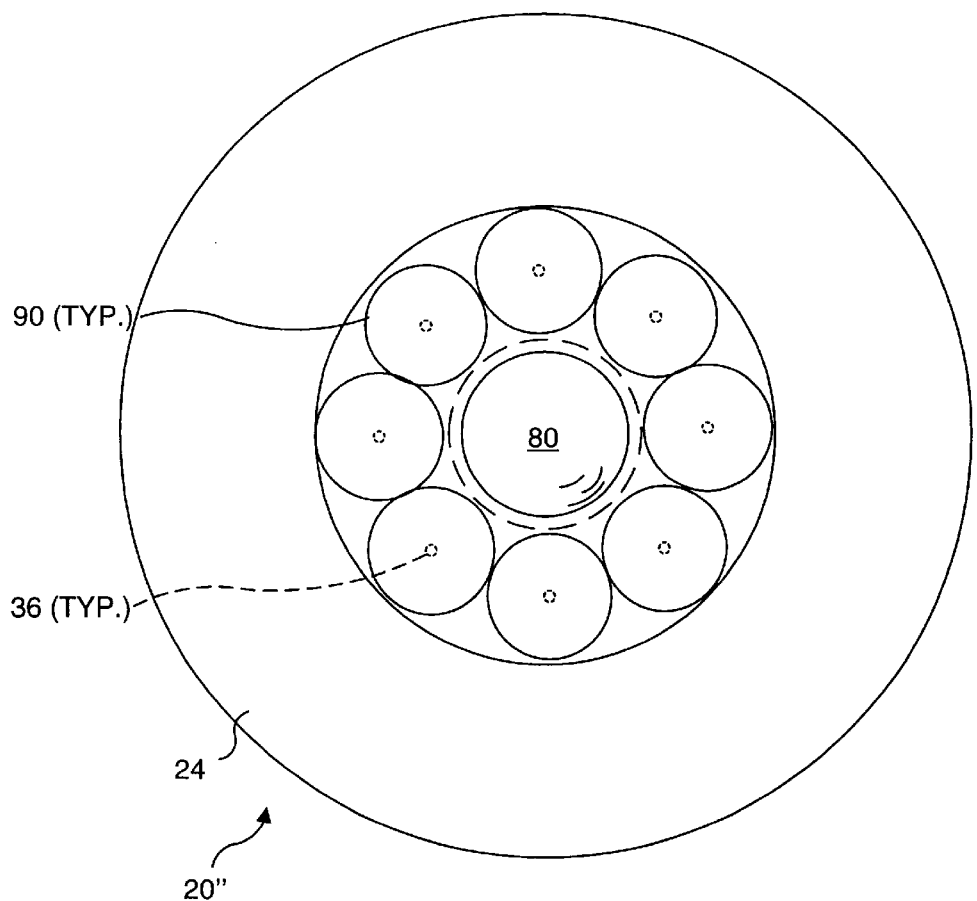
FIG. 8 is a schematic bottom plan view of the third preferred embodiment of the present invention.

FIG. 8 illustrates the circular array formed by the plurality of TIR lenses 90 disposed around gamma probe 80 (or ultrasonic transducer° 30). It should be understood that the TIR lens can be configured to direct the light rays emitted therefrom along diverging, converging, or parallel paths. Accordingly, it is contemplated that a specific configuration of TIR lens having a desired focal length may be selected for use in the therapy head. The TIR lens used may be changed if a different configuration is required to achieve a different focal length.

Figure 9:
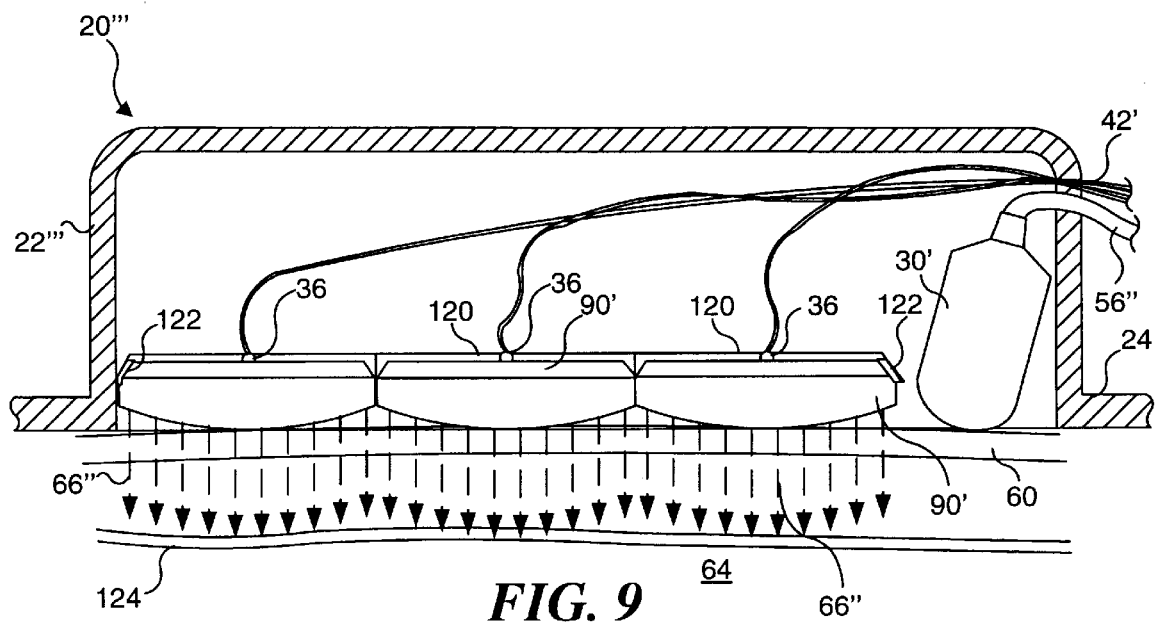
FIG. 9 is a schematic, elevational cross-sectional view of a fourth embodiment of the present invention in which a plurality of light sources are arranged in a linear array.

Yet another embodiment of a therapy head 20''' is shown in FIG. 9. In this embodiment, a housing 22''' is generally elongate and includes a plurality of TIR lenses 90' configured to emit light rays 66" along generally parallel paths. Coupled support rings 120 are connected to the interior surface of housing 22''' and include tabs 122 that fold around the periphery of each TIR lens for supporting TIR lenses 90' within housing 22'''. Adjacent one end of this linear array is disposed an ultrasonic transducer 30', and it is used for producing a signal that can be employed for imaging an internal treatment site to which light therapy is to be or is being applied by light sources 36. The light is focused along generally parallel paths 66" so that the light therapy provided by the linear array of light sources 36 in this embodiment extends along a rather elongate path that is suitable for treating a diseased blood vessel 124. FIG. 9 thus illustrates the substantially linear light therapy pattern produced thereby, which is suitable for treating correspondingly shaped treatment sites. While not shown in this figure, leads 42', and cable 56" extend to the image display/power supply. It is also contemplated that an additional ultrasonic transducer (not shown) might be provided at the opposite end of housing 22''' and can be accommodated within its interior simply by making the housing longer, as appropriate. Use of two such ultrasonic transducers would be more efficient in providing imaging of the elongate treatment site within a patient's body, such as that represented by diseased blood vessel 124.

Figure 10:
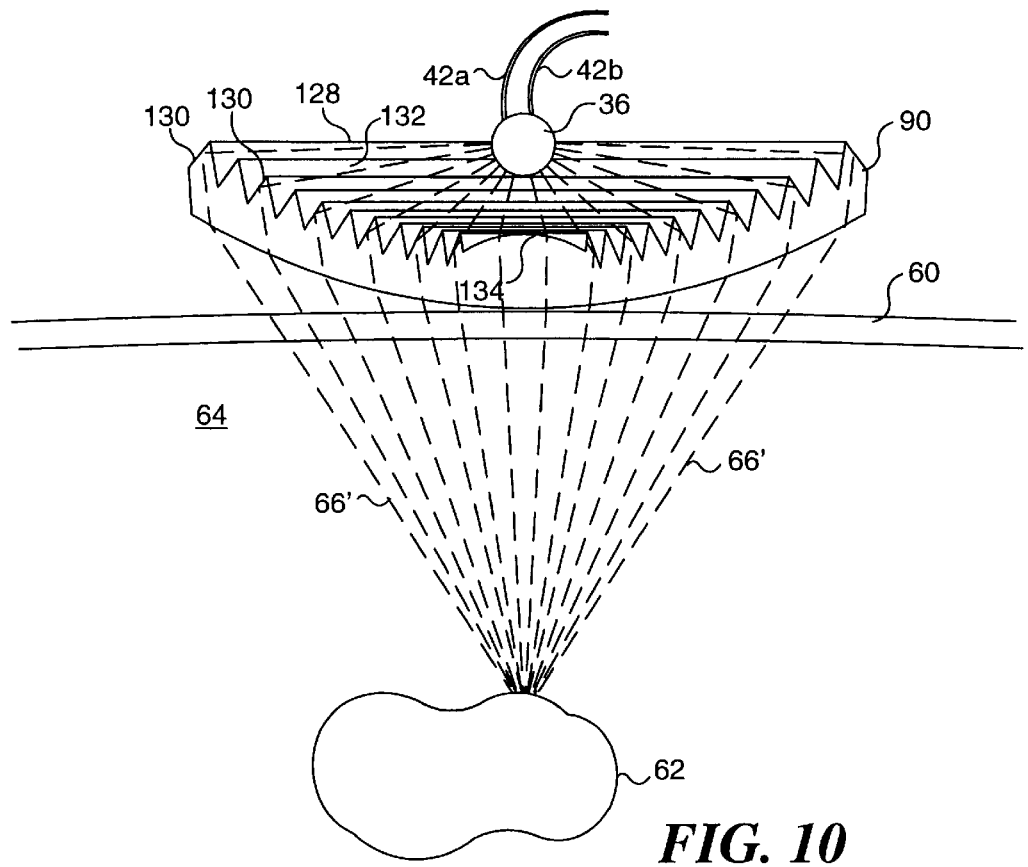
FIG. 10 is a greatly enlarged, schematic cross-sectional elevational view of a totally internally-reflecting lens and LED, illustrating how light emitted by the LED is focused onto an internal tumor.
Figure 11:
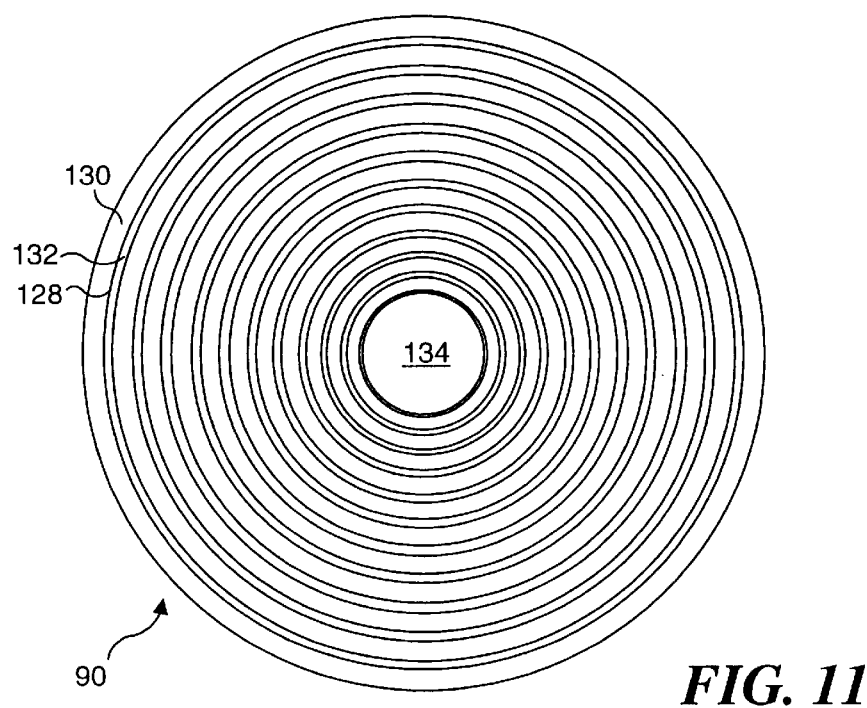
FIG. 11 is a schematic top plan view of the totally internally-reflecting lens of FIG. 10.

Details of TIR lenses 90 are illustrated in FIGS. 10 and 11. While a specific embodiment of a TIR lens appropriate for use in the present invention is illustrated in these and other figures already discussed above, it will be apparent that other configurations of these devices can be employed in connection with the present invention for focusing and directing the light emitted by light sources 36 to achieve the desired directivity and depth of treatment required to properly administer PDT to specific internal treatment sites. A much more complete disclosure of TIR lenses is provided in U.S. Pat. Nos. 4,337,759; 5,404,869; and 5,806,855; the drawings and disclosures of which are hereby specifically incorporated herein by reference.

While the disclosures and drawings of these patents provided all the disclosure required, it will be helpful to briefly discuss the configuration of TIR lens 90, with reference to FIGS. 10 and 11. As shown in FIG. 10, each TIR lens 90 includes a plurality of annular ridges 128, each of which includes a silvered surface 130 and a non-silvered surface 132. When energized by an electrical current conveyed through leads 42a and 42b, light source 36 emits light rays 66' that enter through non-silvered surfaces 132, are internally reflected from silvered surfaces 130 of the concentric ridges, and exit the lower surface of the glass or plastic material comprising TIR lens 90. Since this material has a different index of refraction than air, light rays 66' are focused and directed onto internal tumor 62. By changing the shape of concentric ridges 128, the relative angles between silver faces 130 and non-silvered faces 132, and selecting a material having a desired index of refraction for the TIR lens, it is possible to vary the focal length of the lens, so that light traveling through the lens either travels along diverging paths, parallel paths, or converging paths.

FIG. 11 illustrates the arrangement of concentric ridges 128 in the TIR lens. It will be apparent that a central portion 134 of the TIR lens acts as a conventional refractive lens by focusing the light rays that enter the top surface of this central portion and are not internally reflected. The patents referenced above, which are incorporated herein by reference, disclose many other embodiments of TIR lenses that can readily be adapted for use in connection with the present invention, for directing light on internal treatment sites that have been located and visually displayed using either the ultrasonic transducer or gamma probe, as described above.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for administering light therapy to an internal treatment site within a patient's body, comprising:
   (a) a housing;
   (b) a plurality of light sources arranged in one of a curved and a linear array emitting light within a waveband sufficiently long to penetrate a dermal layer, said light sources being mounted within the housing and emitting light that is generally directed toward a side of the housing; and
   (c) an imaging probe mounted within the housing, said imaging probe being adapted to produce an electronic signal indicative of a location of an internal treatment site within a patient's body for use in positioning the housing and in determining how to direct the light emitted by said light source toward an internal treatment site.

2. The apparatus of claim 1, further comprising a focusing element that controls a direction in which the light is emitted by at least one of the plurality of light sources, said direction being controlled to direct the light emitted by said at least one of the plurality of light sources toward an internal treatment site.

3. The apparatus of claim 2, wherein the focusing element comprises a totally internally-reflecting lens.

4. The apparatus of claim 2, wherein the focusing element comprises a refractive lens.

5. The apparatus of claim 2, wherein the imaging probe comprises one of an ultrasonic probe and a gamma probe, said ultrasonic probe emitting an ultrasonic signal adapted to propagate into a patient's body and to be reflected, the ultrasonic probe producing an electronic output signal useable for creating an image of a treatment site.

6. The apparatus of claim 2, wherein the plurality of light sources are arrayed in a circle about the imaging probe.

7. The apparatus of claim 2, wherein the imaging probe is disposed adjacent to an end of the linear array.

8. The apparatus of claim 2, wherein the plurality of light sources comprise one of a plurality of laser diodes, a plurality of light emitting diodes, a plurality of incandescent light bulbs, a plurality of gas discharge devices, a plurality of laser diodes, and a plurality of polymeric electroluminescent devices.

9. The apparatus of claim 2, wherein the light emitted by the plurality of light sources is adapted to converge on an internal treatment site, producing a substantially greater total light intensity at an internal treatment site than a light intensity of each light source taken separately, thereby minimizing any adverse effect of the light on tissue overlying an internal treatment site.

10. The apparatus of claim 2, further comprising a display device coupled to the imaging probe, said display device being adapted to display an image of an internal treatment site in response to the electronic signal.

11. The apparatus of claim 2, further comprising a power supply that provides a plurality of intermittent pulses of electrical current to energize the plurality of light sources so that the plurality of light sources produce corresponding intermittent light pulses that are directed toward an internal treatment site.

12. The apparatus of claim 2, further comprising an auxiliary imaging probe adapted to produce a signal used to image an internal treatment site, by applying the auxiliary imaging probe to a different position on a patient's body than the housing.

13. The apparatus of claim 1, further comprising a plurality of lenses having different focal lengths, a specific one of the plurality of lenses being selected for its focal length, to focus light emitted by the light source onto an internal treatment site.

14. A method for administering light therapy to an internal treatment site within a patient's body, comprising the steps of:
   (a) administering a photoreactive agent to a patient, said photoreactive agent having a characteristic light absorption waveband and being preferentially absorbed by abnormal tissue;
   (b) providing an imaging device that is integral with a plurality of light sources and produces a signal used for imaging abnormal tissue at the internal treatment site, said light sources emitting light in a waveband corresponding to the characteristic light absorption waveband of the photoreactive agent, said waveband including wavelengths sufficiently long to penetrate through a dermal layer of the patient to the internal treatment site;
   (c) determining a location of the abnormal tissue at the internal treatment site within the body of the patient with the imaging device, by viewing an image of the abnormal tissue at the treatment site developed in response to the signal produced by the imaging device; and
   (d) energizing the light sources to administer light therapy to the internal treatment site at the location determined with the imaging device.

15. The method of claim 14, further comprising the step of focusing the light emitted by the light sources onto the abnormal tissue at a depth within the patient's body determined by viewing the image developed in response to the signal from the imaging device.

16. The method of claim 14, further comprising the step of using the imaging device to monitor a condition of the internal treatment site after light has been administered thereto with the light sources.

17. The method of claim 14, further comprising the step of changing a direction in which light emitted by the sources is directed so that the light is directed onto the internal treatment site.

18. The method of claim 17, wherein the step of changing the direction is done by moving a lens through which the light emitted by the light sources passes.

19. The method of claim 14, wherein the photoreactive agent is specifically targeted at the abnormal tissue by including a binding agent that selectively links the photoreactive agent to the abnormal tissue, but not to normal tissue.

20. The method of claim 14, further comprising the step of intermittently energizing the light sources so that it produces pulses of light.

21. The method of claim 16, further comprising the step of providing an auxiliary imaging device that is used to produce a signal for developing an image of the internal treatment site from a different position on the patient's body than the imaging device.

22. The method of claim 14, further comprising the step of providing the plurality of light sources arranged in one of a curved and a linear array.

23. The method of claim 22, wherein the plurality of light sources are arranged in a circle around the imaging device.

24. The method of claim 22, wherein the plurality of light source comprises one of a plurality of laser diodes, a plurality of light emitting diodes, a plurality of incandescent light bulbs, a plurality of gas discharge devices, a plurality of laser diodes, and a plurality of polymeric electroluminescent devices.

25. The method of claim 14, further comprising the step of providing a plurality of refractive lenses having different focal lengths, to vary a focus of the light emitted by the light sources.

26. The method of claim 14, further comprising the step of providing a totally internally-reflecting lens to change at least one of a focus and a direction of the light emitted by the light sources.

27. The method of claim 22, further comprising the step of providing a different totally internally-reflecting lens for each of the plurality of light sources, to change at least one of a focus and a direction of the light emitted by each of the plurality of light sources.

28. The method of claim 14, wherein the imaging device comprises one of an ultrasound probe and a gamma probe.

\* \* \* \* \*